United States Patent [19]

Gancy

[11] Patent Number: 4,511,485

[45] Date of Patent: Apr. 16, 1985

[54] NONPOLLUTING SALTS AND METHOD OF MAKING SAME

[76] Inventor: Alan B. Gancy, 265 Robineau Rd., Syracuse, N.Y. 13207

[21] Appl. No.: 486,853

[22] Filed: Apr. 20, 1983

Related U.S. Application Data

[63] Continuation-in-part of Ser. No. 319,473, Nov. 9, 1981, abandoned.

[51] Int. Cl.$^3$ ............... C09K 3/18; C01F 5/00; C01F 11/00; C07C 51/41
[52] U.S. Cl. ................... 252/70; 252/381; 252/385; 252/387; 423/421; 423/497; 562/607; 562/608; 23/293 A; 23/304; 106/13
[58] Field of Search ............ 252/70, 381, 385, 387; 423/421, 497; 562/607, 608; 23/293 A, 304; 106/13

[56] References Cited

U.S. PATENT DOCUMENTS

| | | | |
|---|---|---|---|
| 1,958,034 | 5/1934 | Collings | 252/70 |
| 3,906,140 | 9/1975 | Capes | 252/70 |

OTHER PUBLICATIONS

Gmelin's Handbuch der Anorganischen Chemie, 8, Auflage Calcium, Teil B, Lieferung 3, Verlag Chemie, GmbH, Wienheim, 1961.

Gnatyuk et al., "Study of Calcium Acetate Solubility in Aqueous Solutions of Sodium and Calcium Chlorides", Khim. Prom-St., Ser: Khlornaya Prom-St. 1981 (4), 24–8 (Chemical Abstracts 96(8) 58661q).

*Primary Examiner*—John E. Kittle
*Assistant Examiner*—Robert A. Wax
*Attorney, Agent, or Firm*—Austin R. Miller

[57] ABSTRACT

A reduced pollutant-containing salt mixture and method of making same is provided wherein a salt mixture partially comprised of calcium acetate and partially comprised of at least one other pollutant salt is produced by mixing a pollutant salt-containing solution and a calcium acetate-containing solution and converting said mixture into a solid salt containing both the pollutant salt and the nonpollutant calcium acetate. A process option involves chemically reacting calcium chloride and calcium acetate in a calcium chloride-to-calcium acetate mole ratio in the range from 0 to 1 to produce a non-deliquescent salt. A further process option includes mixing either dry calcium chloride or dry sodium chloride with dry calcium acetate to obtain a reduced pollutant-containing salt mixture.

30 Claims, 1 Drawing Figure

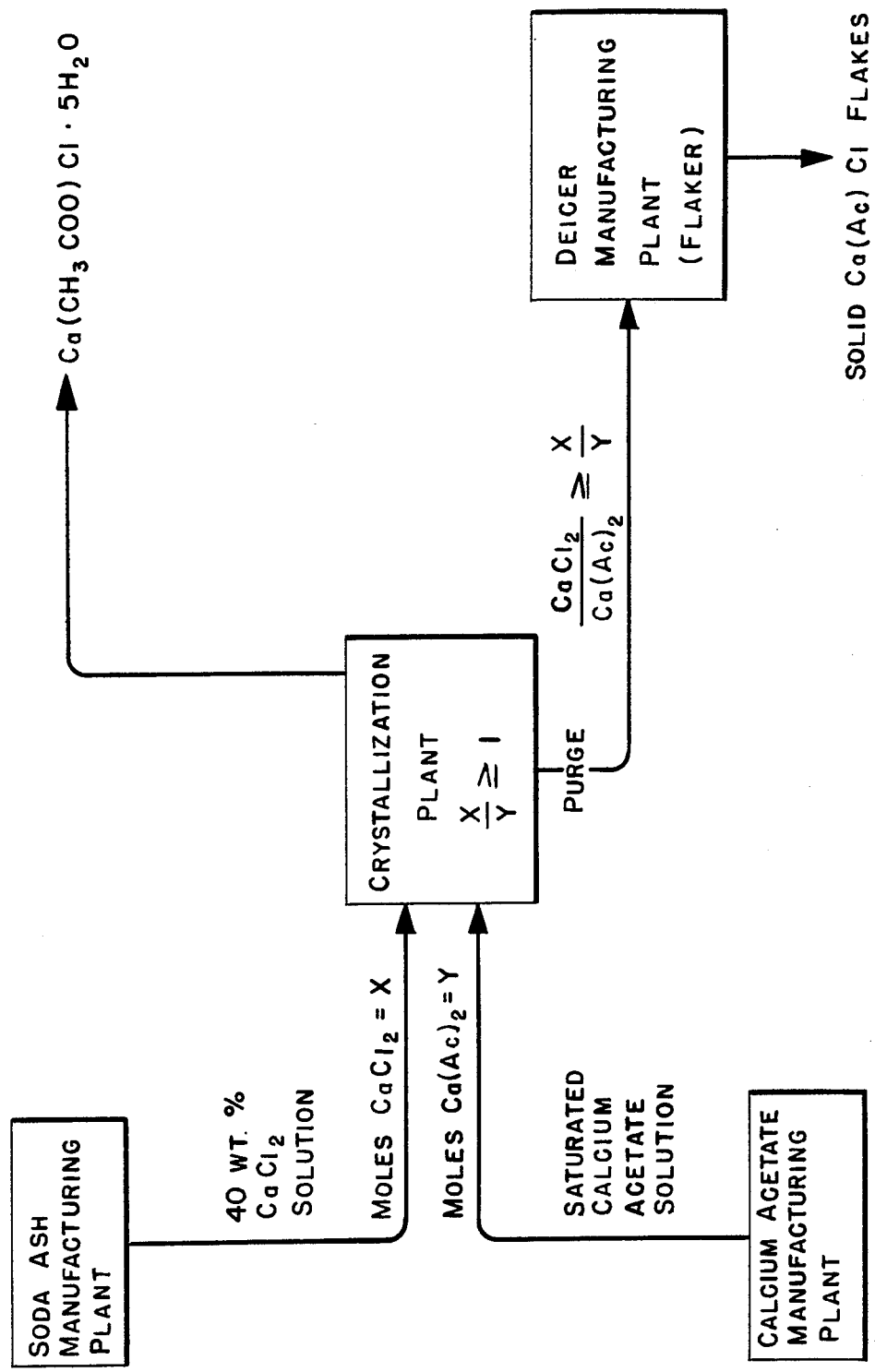

NONPOLLUTING SALTS AND METHOD OF MAKING SAME

This is a continuation-in-part of application Ser. No. 319,473 filed Nov. 9, 1981, now abandoned.

The subject matter of the present invention is related to that described in my copending applications Ser. Nos. 316,816 and 333,037.

BACKGROUND OF THE INVENTION

Field of the Invention

Sodium chloride and calcium chloride are the most common road deicing salts in use today. Sodium chloride is somewhat less expensive due to its high deicing efficiency and the wide distribution of natural deposits throughout the United States. Sodium chloride occurs naturally in a substantially pure state and hence needs only to be mined and ground to the appropriate particle size for storage, shipment and use.

On the other hand, calcium chloride is widely used as a road deicer and also as a antidusting agent for roads in the summertime. Calcium chloride is produced in large quantities as a co-product of the Solvay process for manufacturing soda ash.

Because sodium chloride and calcium chloride are nominally the least expensive road deicing salts, they are the most widely used road deicers in the United States. Annual use of sodium chloride for road deicing in the U.S. exceeds 9,000,000 tons.

Unfortunately, it has recently come to light through environmental studies that the costs of buying and applying sodium chloride and calcium chloride road deicers are misleading indices of the total cost of using these deicers. It has been estimated that damage to vehicles and highway structures through corrosion, and damage to flora, fauna and water supplies inflates the true cost to 14–22 times the nominal cost of manufacturing sodium chloride salt.

Various federal agencies in recent years have been advocating the replacement of calcium chloride and sodium chloride as road-treating agents. To date, there are no known cheap and environmentally acceptable alternative deicers to sodium chloride or calcium chloride.

Sodium is considered an environmental pollutant and chloride ions greatly contribute to the corrosion of metallic surfaces. In rural areas a higher proportion of chlorine in a road deicing agent may be tolerated, whereas in urban or suburban areas a lower proportion of chlorine in deicing agents is desired. Thus, there has been a need in the art for a deicing agent having a versatile and variable chlorine content for use in different environmental areas.

One end result of the efforts to find a cheap and environmentally safe road deicer culminated in a report by Bjorksten Research Laboratories which developed a salt known as calcium magnesium acetate as a substitute for sodium chloride. Unfortunately, the Bjorksten calcium magnesium acetate salts showed a tendency to attack portland cement concrete, possibly due to the acid content of those salts. The problem of calcium acetate and calcium magnesium acetate containing undissociated acetic acid was addressed in my copending application Ser. No. 316,816.

A major obstacle in the use of pure calcium acetate road deicing salt is its high cost of manufacture. This high cost of manufacture is due to the high cost of the raw material acetic acid needed to produce calcium acetate. Until an inexpensive source of acetic acid is developed, the prospects for commercial development of calcium acetate, as a road deicing agent, are not promising. Thus, there has been a further need in the art for a method of producing and using calcium acetate road deicing salts which makes calcium acetate economically viable as a substitute for either calcium chloride or sodium chloride.

Furthermore, both technical grade calcium chloride and commercial grade calcium chloride ($CaCl_2.2H_2O$) are deliquescent. This can pose serious problems in the shipping and handling of the solid crystals, making it necessary to isolate the crystals from water in the atmosphere. Thus, it is another important object of the present invention to provide a road deicing agent which is non-deliquescent and hence does not present these difficult handling, shipping and storage problems.

It is also an important object of the present invention to provide an environmentally safe, yet commercially priced road deicing salt as a substitute for either sodium chloride or calcium chloride.

It is another important object of the present invention to provide a liquid freezing-point depressing agent having good handling, shipping and storage properties and which is environmentally safe.

SUMMARY OF THE INVENTION

A reduced pollutant-containing salt for use in applications such as road deicing and liquid freezing-point depressing is provided comprising a mixture of nonpolluting calcium acetate and a polluting salt such as sodium chloride or calcium chloride for examples.

A reduced pollutant-containing salt is provided comprising a mixture of calcium acetate and another salt or salts.

A further embodiment of the present invention consists of a deicing and liquid freezing-point depressing agent comprising a mixture of calcium acetate and either calcium chloride and/or sodium chloride.

A still further embodiment of the present invention consists of a road deicing agent containing calcium chloride acetate.

A process of making a reduced pollutant-containing salt for use in applications such as road deicing and liquid freezing-point depressing comprises mixing a calcium chloride-containing solution and a calcium acetate-containing solution, removing essentially all undissociated acetic acid from the mixed solution and converting the mixture into solid salt containing both calcium chloride and calcium acetate.

Another option of the above-described process comprises adjusting the pH of the mixed solution to a value of about 7–8. The steps of removing essentially all undissociated acetic acid and adjusting the pH of the mixed solution are more fully described in my copending application Ser. No. 333,037, now issued as U.S. Pat. No. 4,377,488 which is incorporated herein by reference.

A further option of the above-described process comprises an additional step of crystallizing at least a portion of said solution mixture in order to produce a higher purity product either for deicer applications or for other end-use applications where higher purity is desired.

A further embodiment of the present invention comprises mixing sodium chloride and calcium acetate salts having substantially the same particle size distribution and particle density.

Although specific compositions and method steps embodying the invention have been selected for illustration in the drawing and although specific terminology will be resorted to in describing those steps in the specification which follows, their use is not intended to define or to limit the scope of the invention, which is defined in the appended claims.

BRIEF DESCRIPTION OF THE DRAWING

FIG. 1 is a schematic representation of one specific embodiment of the present invention.

DESCRIPTION OF THE PREFERRED EMBODIMENTS

As a relatively nonpolluting substitute for road deicing salts, such as calcium chloride and sodium chloride, I have discovered the synthesis and use of calcium chloride acetate [$Ca(CH_3COO)Cl$ or "CCA"].

Replacement of calcium chloride with CCA as a road deicer results in reducing the quantity of chloride absorbed by the environment by 50% in order to perform an equivalent amount of deicing.

Furthermore, based on an equiosmolar requirement, replacement of sodium chloride with CCA reduces the amount of chloride going into the environment by one third. Such reductions in the amount of chloride being absorbed by the environment are meaningful. A further pollution reduction feature is the tremendous reduction in the amount of sodium, a serious environmental pollutant, added to the environment.

The chloride ion is known to be highly corrosive. On the other hand, calcium acetate is a corrosion inhibitor. Therefore, the corrosiveness of calcium chloride acetate will be much less than that of calcium chloride on an equivalent chloride basis. Thus, two moles of calcium chloride acetate are less corrosive than one mole of calcium chloride. Similarly, one mole of calcium chloride acetate is less corrosive than one mole of sodium chloride. In addition, as was pointed out above, only two thirds of the amount of chlorine, as calcium chloride acetate, is required to do the equivalent deicing work as the chlorine in sodium chloride. Thus, with a lower corrosiveness coupled with a lower dosage required to do the equivalent deicing work, the combined overall effects are a greatly reduced corrosion problem and a greatly reduced chloride pollution problem when using calcium chloride acetate.

The compositions of my calcium chloride acetate road deicing mixtures can range from almost 100% calcium acetate to almost 100% calcium chloride. The proportion of calcium chloride to calcium acetate in the deicing agent is determined by a number of factors, including market demand and pricing requirements of the deicing product, and the level of sodium and chloride pollution which may be tolerated in a particular area. For example, in rural areas, a higher calcium chloride proportion may be tolerated than in urban and suburban areas where a higher proportion of calcium acetate is desirable. Thus, the flexibility and versatility of the calcium acetate-calcium chloride and/or -sodium chloride mixtures is readily apparent from both a pricing standpoint and a pollution control standpoint. Although use of the chloride ion, the more objectionable species in the road deicers, is not totally eliminated, calcium chloride acetate deicing agents present a viable strategy as an interim pollution control measure until either the cost of producing calcium acetate can be reduced or until legislation is enacted proscribing the use of less expensive polluting salts such as sodium chloride and calcium chloride.

A number of novel processes are employed in producing calcium chloride acetate salt compounds. For example, calcium chloride and calcium acetate liquors, such as a 40 wt. % calcium chloride solution as it is produced in the Solvay process for manufacturing soda ash and a substantially saturated calcium acetate solution as is taught in the process of my copending application Ser. No. 333,037, may be simply blended and then converted to solid salt containing both calcium acetate and calcium chloride.

The final mixture of the calcium acetate and calcium chloride solutions is typically sent to a flaking apparatus to convert the mixed solution into solid flakes for applications such as road deicing. Alternatively, the calcium acetate solution may be dried to produce a granular solid whose size distribution and particle density closely approach that of rock salt. This close matching minimizes segregation of solid calcium acetate and sodium chloride when these solids are blended for use as a road deicing agent.

In addition to road deicing, the liquid freezing-point depressing effects of the calcium chloride acetate compounds make them suitable for uses such as freeze-proofing water used in fire pails and other applications, tractor tire weighting, refrigeration applications using brines of calcium chloride acetate and water, freeze-resisting of residual water on coal and ores, and as a cold weather concrete additive.

Referring to FIG. 1, a plant operation is schematically diagrammed utilizing one specific embodiment of the present invention. Calcium chloride is produced as a co-product of the Solvay process for the manufacture of soda ash.

Typically, the calcium chloride is produced as a 40 wt. % solution. Such a solution may then be piped directly to a crystallization operation where it is mixed with a substantially saturated solution of calcium acetate as is produced in the processes of my copending application Ser. No. 333,037.

I have discovered that the proportion of calcium chloride to calcium acetate in the crystallization operation should be greater than or equal to one, preferably greater than one.

The mixed solution of calcium chloride and calcium acetate is then typically fed to a closed, lagged vessel maintained under negative pressure in order to produce substantially pure hydrated crystals of calcium chloride acetate. Typically, the crystallization product has the empirical formula:

$$Ca(CH_3COO)Cl.6H_2O$$

Surprisingly, I have discovered that when the calcium chloride-to-calcium acetate mole ratio charged to the crystallization operation is greater than one, the calcium chloride acetate hexahydrate crystals formed during vacuum evaporation are larger and better formed. This hexahydrate product may then be calcined to form either a lower hydrate, or an anhydrous product.

Since only a portion of the mixed solution is converted into crystals in the vacuum evaporation process, the remaining portion of the mixture (or purge) now has a calcium chloride-to-calcium acetate ratio somewhat greater than that which was mixed in the crystallization operation (due to the removal of Ca(CH$_3$COO)Cl.6H$_2$O crystals). The purge solution is then typically sent to a deicer manufacturing plant where the solution, after appropriate adjustment of the acetate-to-chloride ratio, is charged to a flaking apparatus which typically comprises a heated rotating drum or a heated stainless steel belt. In the flaking operation the purge solution is converted to solid salt particles containing both calcium chloride and calcium acetate.

In contrast to the teachings of established chemical treatises, I have surprisingly discovered that a 1:1 mole ratio solution can be heated to complete dryness and the crystalline product is readily soluble in water. Even more astonishing however is the fact this crystalline product is non-deliquescent. This means that my novel salt products may be shipped in non-airtight containers since there is no danger of absorbing water from the atmosphere with the resultant liquefaction of the salt crystals as is the case with both pure calcium chloride and calcium chloride dihydrate (the predominant form of commercial grade calcium chloride). As a result my relatively non-polluting salt products may be shipped and stored more cheaply than calcium chloride.

My experiments have shown that all of my novel calcium chloride acetate compositions produced according to the processes described herein and having a calcium chloride-to-calcium acetate mole ratio ranging from 0 to unity are non-deliquescent. These compositions may be dried in the form of flakes or other forms as desired. Such solids may be rendered partially or completely anhydrous by calcining. Furthermore, they may be stored and shipped without the problem of caking due to absorption of atmospheric moisture.

Further, experiments indicate that when the above-identified mole ratio exceeds unity by about 20% (ratio of calcium chloride-to-calcium acetate is about 6/5) the salt can be substantially completely dehydrated. While such a salt is not deliquescent according to strict technical definitions, precautions during storage and shipping of the product to limit exposure to atmospheric moisture may be necessary. Of course, such products, even if deliquescent, may be stored in special containers like those used to package calcium chloride.

Still further experiments have shown that when the calcium chloride-to-calcium acetate mole ratio greatly exceeds unity, for example by greater than 50%, storage and packaging precautions similar to those used in the packaging of calcium chloride are required.

A comparative study of a 1:1 and a 4:1 calcium chloride-to-calcium acetate mole ratio solutions was performed. The crystals in the 4:1 solution formed much more quickly than those in the 1:1 solution. However, the 4:1 solution crystals were significantly blockier. That is to say the width-to-length ratio was much higher than the crystals of the 1:1 solution. Furthermore, the 4:1 solution crystals did not bundle as did the crystals in the 1:1 solution.

From my experiments I have discovered that the feed to the crystallization operation should have a calcium chloride-to-calcium acetate mole ratio greater than one in order to produce large, well formed crystals which may be handled in an industrial setting.

Although this invention has been described in connection with specific forms thereof, and with respect to specific steps of the methods herein involved, it will be appreciated that a wide variety of equivalents may be substituted for those specific elements shown and described herein, that certain features may be used independently of other features, and that certain parts and method steps may be reversed, all without departing from the spirit and scope of this invention as described in the appended claims.

I claim:

1. A salt mixture having good water solubility comprised of calcium acetate, magnesium acetate and calcium chloride.

2. A non-deliquescent salt mixture having good water solubility comprised of calcium acetate, magnesium acetate and calcium chloride wherein the mixture has a mole ratio of calcium chloride-to-calcium acetate ranging between 0 and 1.0.

3. A salt mixture comprised of magnesium acetate and non-deliquescent calcium chloride acetate having good water solubility.

4. A salt mixture having good water solubility comprised of calcium acetate, magnesium acetate and sodium chloride.

5. A salt mixture having good water solubility comprised of calcium acetate and sodium chloride, wherein the calcium acetate and the sodium chloride have substantially the same particle size and density.

6. The non-deliquescent salt as described in claim 3 wherein the salt has a mole ratio of calcium chloride species-to-calcium acetate species substantially equal to unity.

7. The salt as defined in claim 3, wherein said calcium chloride acetate is anhydrous.

8. The salt mixture as defined in claim 1, wherein the mixture is a liquid freezing-point depressing agent.

9. The salt mixture as defined in claim 1, wherein the mixture is a deicing agent containing substantially no undissociated acetic acid.

10. A process of making non-deliquescent calcium chloride acetate salt having good water solubility, comprising the steps of:
   a. blending a calcium chloride-containing solution and a calcium acetate-containing solution to form a liquor;
   b. crystallizing at least a portion of the liquor to form calcium chloride acetate salt; and
   c. converting at least a portion of any remaining non-crystallized liquor into solid calcium chloride acetate.

11. A deicing process comprising applying the solid calcium chloride acetate made according to the process of claim 10 to ice.

12. A process for lowering the freezing-point of a liquid comprising adding the solid calcium chloride acetate made according to the process of claim 10 to the liquid.

13. The process as defined in claim 10, wherein magnesium acetate is present in the liquor.

14. The process as defined in claim 12, wherein the liquid is water.

15. The process as defined in claim 10, wherein the liquor has a mole ratio of calcium chloride-to-calcium acetate in the range between 0 and 1.

16. The process as defined in claim 10, wherein step (b) comprises vacuum crystallizing said portion of the liquor.

17. The process as defined in claim 15, wherein said vacuum crystallization comprises feeding said mixture into a lagged, closed vessel maintained substantially under a vacuum.

18. The process as defined in claim 10, wherein said calcium acetate-containing solution is saturated.

19. The process as defined in claim 10, wherein said calcium chloride-containing solution is a product of a process for manufacturing soda ash containing about 40 wt. % calcium chloride.

20. The process as defined in claim 10, wherein step (b) comprises introducing the liquor into a flaking apparatus.

21. The process as defined in claim 20, wherein said flakes have a diameter in the range from about 0.25 to about 0.75 inches, a thickness in the range from about 0.04 to about 0.1 inches and are substantially disc shaped.

22. The process as defined in claim 20, wherein said flaking apparatus comprises a heated rotating drum.

23. The process as defined in claim 20, wherein said flaking apparatus comprises a heated stainless steel belt.

24. The process as defined in claim 10, including an additional step of removing substantially all undissociated acetic acid from the calcium acetate-containing solution.

25. The process as defined in claim 24, wherein said additional step comprises adjusting the pH of said calcium acetate-containing solution to about 7–8.

26. In a process of making a deicing agent, the step comprising mixing sodium chloride crystals and non-deliquescent, readily water soluble calcium chloride acetate crystals having substantially the same size and density.

27. A method for depressing the freezing-point of a liquid comprising adding to the liquid an effective amount of a salt mixture comprising non-deliquescent calcium chloride acetate having good water solubility and magnesium acetate.

28. A method for depressing the freezing-point of a liquid comprising adding to the liquid an effective amount of a salt mixture comprised of calcium acetate, magnesium acetate and calcium chloride.

29. A method for depressing the freezing-point of a liquid comprising adding to the liquid an effective amount of a salt mixture having good water solubility comprised of calcium acetate, magnesium acetate and sodium chloride.

30. A method for depressing the freezing-point of a liquid comprising adding to the liquid an effective amount of calcium acetate and magnesium acetate.

* * * * *